Figure 1:
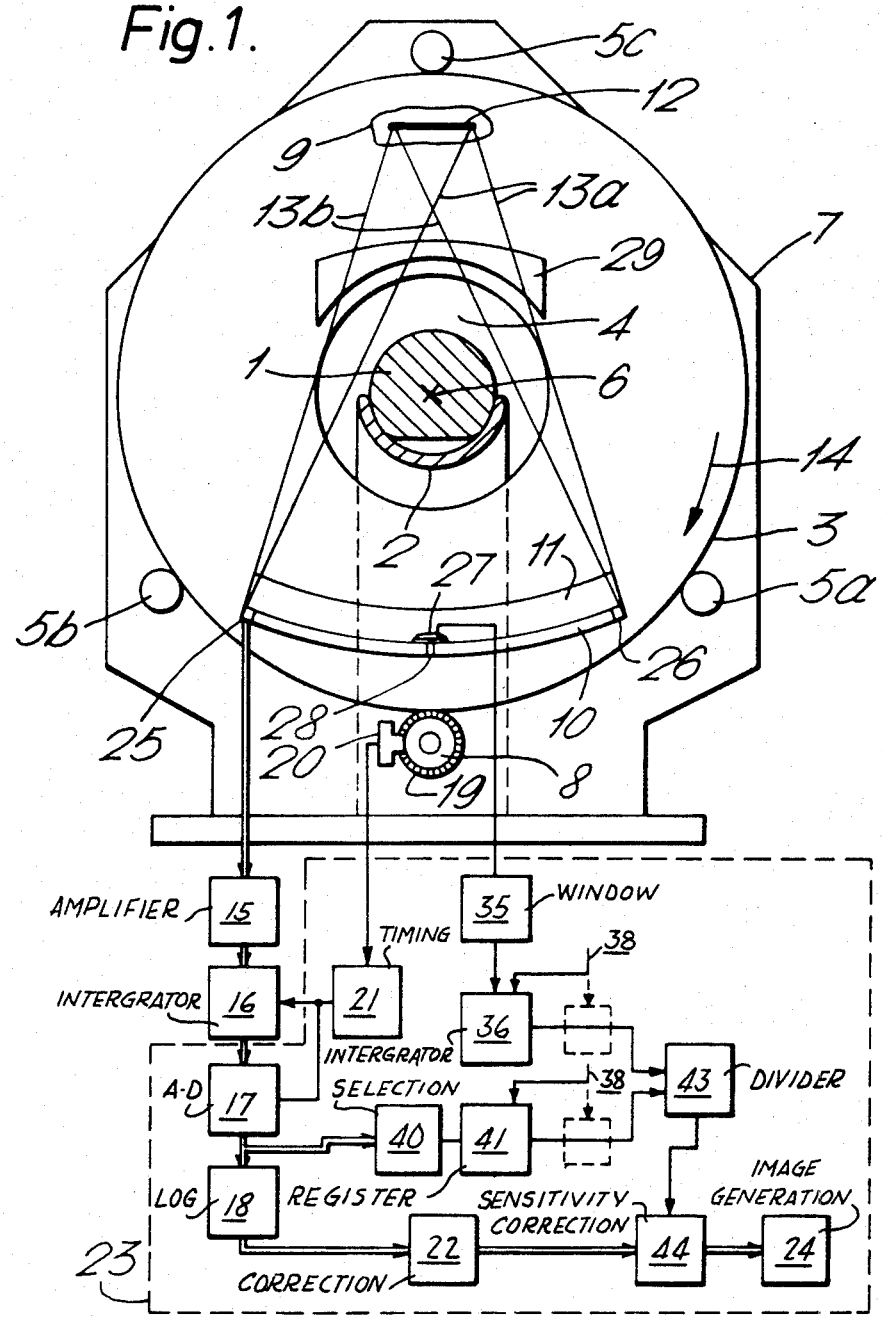

United States Patent [19]

Waltham

[11] Patent Number: 4,472,823
[45] Date of Patent: Sep. 18, 1984

[54] COMPUTED TOMOGRAPHY APPARATUS WITH DETECTOR SENSITIVITY CORRECTION

[75] Inventor: Richard M. Waltham, London, England

[73] Assignee: U.S. Philips Corporation, New York, N.Y.

[21] Appl. No.: 470,888

[22] Filed: Feb. 28, 1983

[30] Foreign Application Priority Data

Mar. 17, 1982 [GB] United Kingdom ................ 8207812
Jan. 24, 1983 [GB] United Kingdom ................ 8301898

[51] Int. Cl.³ .............................................. A61B 6/00
[52] U.S. Cl. .................................... 378/19; 364/414; 378/901
[58] Field of Search ................. 378/19, 901; 364/414

[56] References Cited

U.S. PATENT DOCUMENTS 4,071,760 1/1978 Le May ................................ 378/19
4,260,895 4/1981 Schittenhelm ...................... 378/19

Primary Examiner—Alfred E. Smith
Assistant Examiner—T. N. Grigsby
Attorney, Agent, or Firm—Jack E. Haken

[57] ABSTRACT

In a rotary fan beam computed tomography apparatus using recurrent relative displacement between the source and detectors (e.g. a deflected spot X-ray tube 9) for the recalibration (22) of detectors in chain-like sequences across the detector array 10 by successive pairwise common-path sensitivity comparisons starting from a terminal detector 25, 26, each sequence normally involves 30 or more successive comparisons, and consistent but unpredictable errors are found to occur, leading to incorrect Houndsfield values in the computed image matrix (24).

The improvement comprises locating at least one radiation transparent detector 27 of high stability in front of the array 10 at an intermediate point and using the output to further correct the chain-corrected detector sensitivity values.

A detector 27 comprising a plastics scintillator optically coupled to a photomultiplier is described, whose output pulses are counted (36) during a rotational scan and compared with the mean corresponding measurement from detectors 28 lying behind the detector 27, to form a sensitivity ratio (43). From a corresponding ratio and data derived during calibration, a measured sensitivity value for detectors 28, is determined for each scan and is compared with the corresponding chain-corrected sensitivity value to generate a further sensitivity correction value which is then distributed among the detectors of the comparison sequence (44).

10 Claims, 7 Drawing Figures

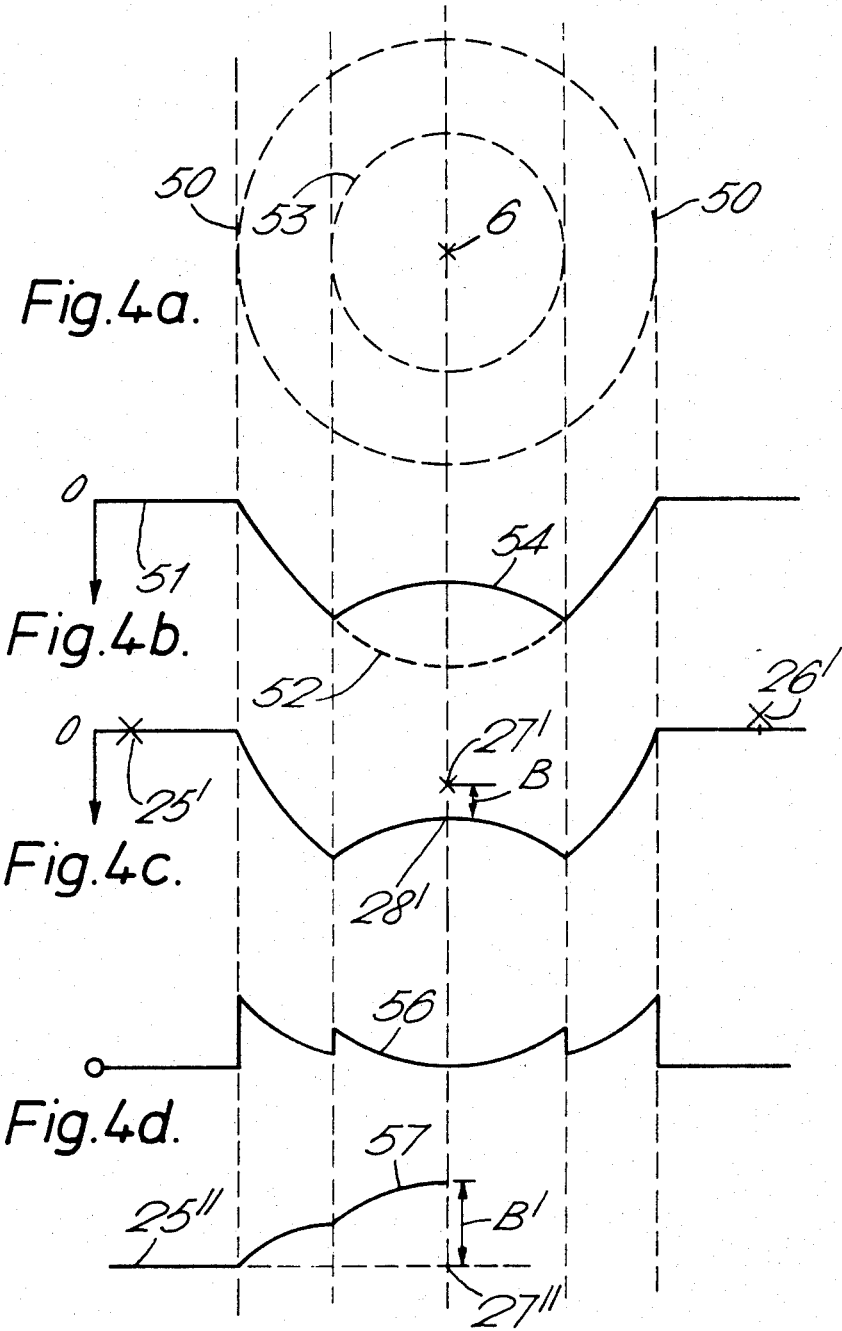

COMPUTED TOMOGRAPHY APPARATUS WITH DETECTOR SENSITIVITY CORRECTION

This invention relates to computed tomography apparatus for measuring the attenuation of penetrating radiation along each of a plurality of measurement paths directed in the plane of a predetermined planar section of a body under examination, and computing therefrom the distribution of local attenuation and hence a physical variable such as density in the body section, including a source of penetrating radiation arranged to irradiate the body section with a fan-shaped beam coplanar with the body section, an array of detectors arranged to receive said radiation after passing through the body section, the array extending so that a terminal detector receives direct radiation from the source unattenuated by the body section, the source and detectors being displaceable relative to one another so that radiation from a respective measurement path in relation to the body section, can be measured in succession by different detectors of the array, and signal processing means arranged to receive measurement signals from the detectors, to compare signals provided by different detectors of the array from a measurement of radiation from substantially the same respective measurement path in relation to the body section, so as to determine the sensitivity of a detector relative to that of another, and to repeat the comparison in respect of an overlapping succession of respective pairs of detectors thereby to establish at least one calibration sequence of detectors along the array, whose sensitivities are determined and corrected in a pair-wise succession relatively to a said terminal detector, and such apparatus will be referred to herein as computed tomography apparatus of the kind set forth. It should be understood that in such apparatus each measurement path is defined by the momentary position of the source and of a corresponding individual detector element to the detector array in relation to the body section under examination while a corresponding measurement is being made, and will take account of any scanning displacement of the apparatus during a corresponding sampling and integration period.

Examples of rotary scan fan-beam computed tomography apparatus in which the source position is also scanned relative to the detector array to enable the attenuation along substantially the same measurement path in relation to the patient, to be measured by different detectors to determine the relative sensitivities thereof, are described in U.S. Pat. Nos. 4,097,744; 4,010,370; 4,171,476; and 4,178,511; and further detector sensitivity comparison arrangements are described in U.S. Pat. Nos. 4,066,902 and 4,172,978.

By the use of such methods of path-overlap measurement, the sensitivity of overall gain of each detector and amplifier combination, can be compared with, i.e. calibrated relative to, that of a preceding detector along the array and ultimately, after a succession of pair-wise comparisons, it can be defined, i.e. calibrated, relative to that of a terminal detector and amplifier combination of the array which receives radiation directly from the source, meaning in practice via a graded attenuating body, without passing through the body under examination. In practice it is usual to employ a terminal detector at both ends of the array and to apply a "best fit" correction to the calibration sequence.

It should be understood that, for reasons of scan geometry and timing, it is, in general, not possible to correct all the detectors of an array in a single calibration sequence, but that a plurality of interlaced successions of detectors, each succession being referred to herein as a comparison chain, have to be calibrated from a corresponding terminal detector reference point or points. However, it is a simple matter to compare the sensitivities of the respective terminal detectors at a given end of the array, with one another.

In apparatus such as that described in U.S. Pat. No. 4,178,511, for example, the detector calibration applied at the centre of the detector array may be the result of performing 30 or more pair-wise detector comparisons in series. The serial nature of the chain-like calibration process means that consistent errors would tend to accumulate at each comparison, and would be capable of generating a significant measurement error.

Some correction can be effected by precalibrating the detector sensitivities by the use of a standard uniform phantom of the same cross section and mean attenuation as that of an average patient, and applying the chain calibration process to correct variations from the calibrated sensitivities during a patient scan. In principle this approach should provide correction for linear discrepancies. However, it has been found that consistent errors can nevertheless occur in practice causing unacceptable cumulative errors to develop, and such errors may result from non-linear processes.

It is usual to provide a graded attenuating body in the beam path between the source and the body under examination in order to make the outputs from the detectors more similar in magnitude at different points along the array, especially those near the ends of the array when compared with those near the centre. This enables detectors in all parts of the array to operate over similar portions of their working characteristics, reducing the effects of detector non-linearity and also reducing the overall patient dose. The attenuation produced by the graded attenuating body is measured and stored during an initial calibration scan during which, of course, the effects of shifting the source position by scanning the position of the focal spot of the X-ray tube, which entails effectively shifting the source relative to the attenuating body, can also be taken into account.

However, as a consequence, the shift in source position occurring during the source scan from a position in which one detector measures a given path through the body to that position in which a different detector can measure the same path, will in general cause the radiation to traverse a different path through the attenuator, and this can cause a change in the hardness of the beam. In the case of a measurement on a body section which corresponds in shape, etc, with that of a calibrating phantom, this effect of source shift can be included in the initial calibration measurement. However, because attenuation is non-linearly dependent on beam hardness, measurement on a body section which differs significantly from the calibration section in shape and/or in density distribution, can give rise to said consistent form of error in the comparison chain.

It should be understood that such errors can cause artifacts to be generated and will result in errors in the resultant computed image matrix of local absorption values.

It is an object of the invention to provide an improved computed tomography apparatus of the kind set forth, in which the effects of such consistent errors can be reduced or compensated.

According to the invention there is provided a computed tomography apparatus for measuring the attenuation of penetrating radiation along each of a plurality of measurement paths directed to the plane of a predetermined planar section of a body under examination, and computing therefrom the distribution of local attenuation and hence of a physical variable such as density of the body section, including a source of penetrating radiation arranged to irradiate the body section with a fan-shaped beam coplanar with the body section, an array of detectors arranged to receive said radiation after passing through the body section, the array extending so that a terminal detector receives direct radiation from the source unattenuated by the body section, the source and detectors being displaceable relative to one another so that radiation from a respective measurement path in relation to the body section, can be measured in succession by different detectors of the array, and signal processing means arranged to receive measurement signals from the detectors, to compare signals provided by different detectors of the array from a measurement of radiation from substantially the same respective measurement path in relation to the body section, so as to determine the sensitivity of a detector relative to that of another, and to repeat the comparison in respect of an overlapping succession of respective pairs of detectors thereby to establish at least one calibration sequence of detectors along the array, whose sensitivities are determined and corrected in a pair-wise succession relatively to a said terminal detector, characterised in that there is provided at least one reference detector which is substantially transparent to said penetrating radiation, and located in the path of said radiation after passing through the body section, in front of at least one intermediate detector of said array, said signal processing means being further arranged to compare the signal provided by the or each said reference detector, respectively, with that provided by at least one corresponding intermediate detector of the array forming part of a said calibration sequence and receiving radiation after passing through said reference detector, to generate therefrom a corresponding correction signal representative of a cumulative correction error present in the relevant span of the calibration sequence, and to distribute related corrections in respect of the detectors forming said span of the calibration sequence, so as to make stored signals derived from the detector output signals, a more accurate measure of the radiation intensity after passing through the body section and hence of the path attenuation in said body section, than in the absence of the further correction.

The invention is based on the realisation that the relative displacement of source and detector employed in combuted tomography apparatus of the kind set forth, to provide path-overlap detector sensitivity measurements, can give rise to significant and cumulative errors in the detector sensitivity comparison chain, and that such errors can result from non-linear effects, such as beam hardening, which are difficult to compensate by the usual calibration procedures using a standard phantom, because of the variability not only of the shape and size, but also the density distribution of the body sections of different patients. The invention is further based on the unexpected realisation that while measuring the path attenuation profile of a fan spread of radiation to a high degree of accuracy, it is nevertheless possible to locate a substantially transparent reference detector in front of some of the detectors of the detector array, without significantly degrading that accuracy and while providing a useful correction signal which can significantly increase the accuracy of the measurement process.

A substantially transparent reference detector is to be understood herein to mean a detector which permits a useful proportion of the penetrating radiation (e.g. X-rays) incident thereon to pass to those detectors of the measurement detector array situated behind the reference detector such that the computed output image matrix of local attenuation or density (e.g. Houndsfield) values can be maintained within closer limits of accuracy by means of the invention.

Preferably the reference detector should not absorb more than 20% of the incident radiation, and if possible this proportion could with advantage be reduced to or below 10%. However, a detector exhibiting a greater amount of absorption can nevertheless be used usefully in apparatus in accordance with the invention to increase the accuracy of the computed matrix of local values relative to that of apparatus of the kind set forth in which the said reference detector is not present and the invention is not employed.

In an embodiment of the invention the signal processing means is arranged to integrate the respective outputs from a said reference detector and from at least one said intermediate detector of the array which receives radiation after passing through the reference detector, throughout at least the major portion of a rotary measurement scan performed by an assembly comprising the source and the detector array, about the body section under examination, then to form the ratio of the resultant integrals, then to form the product of said ratio and a stored value representing the sensitivity of the reference detector thereby to generate a measured sensitivity value representative of the sensitivity or mean sensitivity of said intermediate detector or detectors, and to determine the difference between said measured sensitivity value and an initially-corrected sensitivity value correspondingly representative of the sensitivity or mean sensitivity of said intermediate detector or detectors as initially corrected using a said calibration sequence, thereby to provide said correction signal representative of a cumulative error present in the relevant span of the calibration sequence.

The reference detector can be formed as to extend along the detector array in front of a backing group of intermediate detectors of the array, and the signal processing means can be arranged to weight the respective outputs of the detectors forming said backing group with respect to said integration, and to correspondingly weight the respective detector sensitivities as initially corrected using said calibration sequence prior to forming said initially-corrected sensitivity value therefrom, the weighting respectively applied with respect to each said intermediate detector being dependent on the sensitivity of the reference detector to said radiation passing therethrough via the corresponding measurement path defined by the intermediate detector, relative to the sensitivity thereof in respect of a said measurement path passing centrally therethrough.

In a preferred arrangement for distributing the correction signal among the various detectors, the signal processing means can be arranged to compute a distribution function comprising the integral of the modulus of the slope of a path-attenuation profile generated from detector output signals and a set of corresponding detector sensitivity values as initially corrected using a said calibration sequence, and then to derive said related corrections from said correction signal representative of a cumulative correction error present in the relevant span of the calibration sequence and to distribute said related corrections amongst the detectors forming the relevant span of the calibration sequence in accordance with said distribution function, the value of said distribution function being zero at the start of said relevant span which coincides either with a terminal detector or a further corrected detector sensitivity value which forms the end of a previously processed, i.e. further correct, span.

Figure 2:
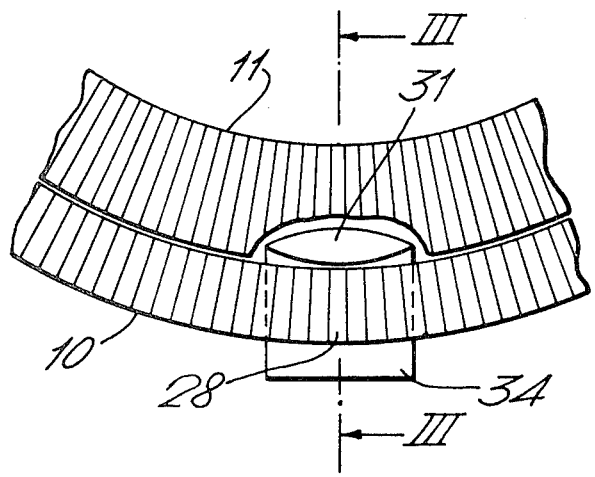
Figure 3:
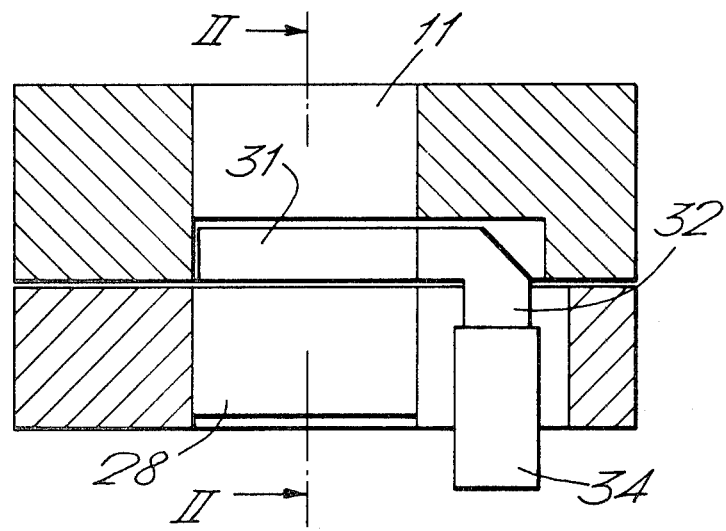

Embodiments of the invention will now be described by way of example, with reference to the accompanying drawings of which:

FIG. 1 schematically illustrates computed tomography apparatus embodying the invention, FIGS. 2 and 3, comprise two sectional details relating to the apparatus shown in FIG. 1, and FIGS. 4a, b, c, d and e, are diagrams and graphs illustrating the operating of the apparatus of FIG. 1.

Referring to FIG. 1, this illustrates diagrammatically an example of computed tomography apparatus of the kind set forth and embodying the invention. In FIG. 1, a transverse section 1 is shown of a body under examination which latter is supported on a patient support 2. The body section 1 to be examined, may be surrounded in conventional manner by water bags (not shown) so that the boundary of the absorption field is rendered approximately circular to facilitate subsequent computation.

The apparatus comprises a rotatable member 3 having a central aperture 4 in which the body section 1 is centrally located by the support 2. The rotatable member 3 bears on rollers 5a, 5b and 5c so as to be rotatable about a central axis 6 which is longitudinal with respect to the body, and perpendicular to the plane of the body section 1, and of the drawing of FIG. 1. The rollers 5 are journalled in a main supporting frame 7 which may take any form suitable to support the apparatus and to allow the necessary rotation. The member 3 is caused to rotate about the axis 6 by means of a drive motor 8 suitably coupled thereto via toothed drive coupling means (not shown), for example a toothed belt engaging peripheral teeth forming part of the member 3.

The rotatable member 3 carries an X-ray source 9, and an array 10 of detectors and associated collimators 11. The detectors are of any suitable type, for example scintillation crystals with associated optical-electrical signal converters such as photodiodes or photomultipliers. The important characteristics required for the detector elements of the array 10, are that they should have a high efficiency in converting X-rays into optical radiation so as to provide a high sensitivity, thus enabling the dose to the patient to be kept to a minimum for a given noise-defined performance limit, and that a high spatial resolution should be provided in the vicinity of the centre of the array.

An example of a convenient form of detector is a caesium iodide scintillator crystal coupled directly to a silicon photodiode. The detector elements in a typical way may number 1000, but the outputs of some of the elements would normally be taken together in groups of two or more towards the ends of the array where less resolution is required.

The X-ray source 9 includes an elongate target-/anode 12 along which the electron beam impact spot is periodically deflected by suitable deflection means (not shown), and the emergent radiation is limited to form a fan-shaped beam 13 directed in the plane of the body section 1 and spanning the detector array 10. The source point of origin of the fan-beam 13, is scanned from the position 13a to the position 13b. Suitable forms of scanned spot X-ray tube are described in U.S. Pat. Nos. 4,002,917 and 4,039,807, and will not be further described. For reasons recounted hereafter, the fan beam must always extend laterally beyond the boundary of the body section 1 to one side, and preferably to both sides, so that a terminal detector element 25, 26 at the end of the array 10, or preferably a respective element at each end of the array, receives direct radiation from the source unattenuated by the body section 1. In the present example the fan beam extends over an angle at 50°, and the scan of the origin of the X-rays along the target is about 4 cms, although it may be more or less than this if desired.

In the present example, the X-ray source 9 is located approximately 60 cms from the central axis 6, with the detectors 10 a further 60 cms on the opposite side of the axis. However, the respective distances from the axis to the source 9, and to the detectors 10, may be equal unequal, if desired. The detector collimators 11 are arranged so that their longitudinal collimating axes intersect at the centre of the anode 12, and the detector array 10 is arranged to conform approximately to a circular arc also centered at the centre of the anode 12, and therefore having a radius of about 120 cms.

In accordance with usual practice, a graded attenuating body 29 is mounted on the rotatable member 3 and located between the X-ray source 9 and the body section 1. Because a scanned-spot source is used the body 29 should be as far from the source 9 and as close to the body section 1 as is practicable to reduce the effects of source shift, although linear effects will tend to be corrected for during the initial calibration process. The attenuating body 29 can alternatively be located between the body section 1 and the detector array 10, where it can equally well compensate for varying mean path attenuation across the body and be less subject to the effects of source shift, but in this position the patient dose will be undesirably increased. As a compromise a respective attenuating body can be disposed at both locations, each effecting a partial compensation.

The radiation output ($I_o$) of the X-ray source is monitored by a stable detector (not shown) which is located on the source side of the usual beam limiting diaphragm (not shown) and outside the path of radiation forming the irradiating fan beam 13a, 13b. The output from the source monitoring detector can be integrated and sampled in conventional manner, converted to digital form and then, if desired, logarithmically converted to facilitate computation so that subsequent multiplication and division can be performed by addition and subtraction, and because attenuation is expressed as the logarithm of an intensity ratio.

In operation, the rotatable member 3 is rotated at a steady speed about the axis 6 by the motor 8 in a clockwise direction indicated by the arrow 14. At the same time the X-ray spot is deflected at a uniform speed from the right hand end of the anode 12, beam 13a, to the left hand end, beam 13b, the electron beam is then interrupted during a flyback period during which the spot deflection is restored to the right-hand end, as shown in FIG. 1. As explained in, for example, U.S. Pat. Nos. 4,010,370; 4,097,744; 4,171,476 and 4,178,511, by selecting an appropriate contradisplacement speed for the X-ray source, each element of the detector array can measure attenuation along a plurality of adjacent measurement paths relative to the body section, which are either parallel to one another or intersect at a virtual point some distance beyond the detector array. The effective width of each measurement path will be defined by the size of the detector element, the size of the X-ray source spot, and the length of the sampling and integration period of the detector output relative to the displacement speed of a notional line joining the source and the detector, as it is scanned across the body section.

The analog output signal from each detector element of the array 10, is applied to a corresponding amplifier 15 and integrator 16, and each integrated output signal is converted to digital form in an analog-digital converter 17, and to logarithmic form in a logarithmic converter 18. The detector signal samping times are synchronised to the rotation of the rotatable member 3 by means of a graticule or a coding disc 19 attached or coupled without backlash to the member 3, and a corresponding optical sensor 20 mounted on the support frame 7 and comprising, conventionally, a light source and a photocell. The photocell output is applied to a timing circuit 21 which generates a detector output sampling pulse which transfers the respective integrator output to the analog-digital converter, resets the integrator and generates a scan position and detector number identification code related to the detector sample. The circuit 21 also synchronises the scan applied to the X-ray source spot to generate the required measurement paths relative to the body section 1, by controlling the source scan relative to the rotation of the number 3 and to the detector sampling times, so that the attenuation along given measurement paths defined in relation to the body section 1, is respectively and successively measured by different detectors to enable the sensitivity of a detector to be determined relative to that of another in a pair-wise manner.

The output signals from the logarithmic converters 18, are fed to a detector signal correcting device, or programmed function, illustrated diagrammatically by a block 22, which forms part of signal processing means 23. The block 22 represents, in effect, means for sorting, storing, selecting and comparing the various detector outputs derived from the corresponding logarithmic converters 18, in order to generate detector sensitivity correction signals and thereby to correct the measurement values relating to corresponding measurement paths through the body section 1, prior to forming and storing corrected path attenuation values and applying these values to conventional computed tomography data processing and image generation means 24, which can also comprise a programmed function of the signal processing means 23. The functions of the block 22 may be performed by dedicated conventional circuit means, or by a suitably programmed operation in the more generalised computing facility employed to compute the output image.

The function of the block 22 is firstly to store detector log output values when a calibration scan is initially performed on a reference body having a uniform radiation absorption distribution similar to that of water, and which may comprise water in a suitable container or a plastic phantom having a circular section similar in size to the section 1 to be measured.

The function of the block 22 is, initially, to store detector log outputs during various calibration scans. Thus a first scan is performed in which the object space within the central aperture of the member 3 is empty and the detector log outputs are stored, together with the corresponding source intensity. This provides a base reference which takes account of the effect of the graded attenuator 29.

A further calibration scan is then carried out using a reference body in place of the body section 1, and having a uniform radiation absorption distribution similar to that of water. The reference body may comprise water in a suitable container or a plastics phantom having a circular section similar in size to the body section 1 to be measured.

Other functions of the block 22 which can be performed either while a body section is being scanned or at a later time, including systematically selecting pairs of detector log output values which have each been measured along the same respective measurement path in relation to the body section, forming a ratio of the two values, i.e. by subtraction of the log values, so as to define the sensitivity of one of the detectors of the pair relative to that of the other, and to repeat the comparison in respect of a succession of respective such pairs of detectors so as to establish a corresponding calibration sequence of detectors along the detector array 10, whose sensitivities are determined and corrected in a pair-wise succession relative to a terminal detector 25 or 26, or preferably both, each of which is arranged so as to receive direct radiation from the source 9 via the graded attenuator 29 but unattenuated by the body section 1 to be measured.

Since the detector signals are conveniently stored as log values the steps of multiplying and dividing required to derive the sensitivity of a detector from the sensitivity of a terminal detector and a product of comparison ratios, can be readily performed by addition and subtraction of corresponding log values.

In the preferred case of using a terminal detector 25, 26, at each end of the detector array 10, one method of sensitivity correction would be to establish two comparison chains for each sequence of detectors, starting at a corresponding terminal detector and finishing with at least one common central detector. In general the chain-corrected sensitivity value for this common detector as determined by the two comparison chains, would not be the same, and the difference between the two values would then be distributed between the chain corrected sensitivity values of the two chains, as additional correction values in accordance with a suitable "best fit" criterion.

It is usual in computed tomography to make a complete radiographic scan of a body section as rapidly as possible so that no significant movement of the patient takes place. This can, if desired, entail storing all the successive raw samples from each of the detectors in a manner such that the corresponding detector and measurement path relative to the body section associated with each sample, will be readily identified for recall at a later time. Corrections can then be made relating to the sensitivity variations of individual detectors and applied to the raw sample data to generate corrected data suitable for computing the output distribution of attenuation coefficients and hence for forming the output image, without the need for slowing down the scan or losing any measurement data.

Up to this point the apparatus is generally similar to that described variously and inter alia in U.S. Pat. Nos.

4,178,511; 4,172,978; 4,171,476; 4,097,744; 4,066,902 and 4,010,370.

In order to counteract cumulative errors which can occur in the chain-corrected sensitivities of detectors situated intermediate the terminal regions of the detector array 10 adjacent the terminal detectors 25 and 26, in accordance with the invention at least one reference detector 27 is disposed in the path of radiation from the source 9, after passing through the body section 1, in front of at least one intermediate detector 28 of the array 10. The reference detector 27 must be substantially more stable than, and have better linearity than the detectors 28 normally employed in the detector array 10. The reference detector 27 must also be substantially transparent to the penetrating radiation employed and it is to be preferred that it should not absorb more than 20% of the radiation incident thereon, and, if possible, not more than 10%. The detector 27 need not, however, have as great an efficiency nor as high a spatial resolution as the detectors 28, in fact the detector 27 can extend in front of several of the detectors 28 in the array 10, and it can be desirable that it should.

A preferred embodiment of the reference detector 27 is illustrated in FIGS. 2 and 3, which relate to an intermediate portion of the detector array 10. The reference detector 27 comprises a plastics scintillator 30 formed of a scintillation plastics material which can generate light photons within a very short interaction time or decay time in response to an incident photon of penetrating radiation. Examples of such a material are manufactured by Nuclear Enterprises of San Carlos, Calif. as NE 102A, NE 106, NE 111 and NE 140, which all appear to have a suitably short decay time.

The scintillator extends transversely across the front of the detector array 10, and is shaped to a uniform cross section of lenticular form in a direction along the array 10 as shown in FIG. 2, so as to extend in front a small number of the detector elements 28 of the array 10, without casting a significant hard shadow at either edge, which would tend to be displaced during a source scan.

In one example the thickness of the scintillator 30 along the beam direction would be 5 mm and the width in a direction along the array 10 about 10 mm. The detector would therefore extend in front of about 11 detector elements in the array 10.

The entire surface of the scintillator 30 with the exception of one end 31, is coated with a thin layer of optically reflective material which does not add substantially to the absorption of the X-radiation, suitably aluminium. The scintillator 30 is coupled at the end 31, via a light guide 32, suitably of a transparent acrylic plastics material with similarly reflective outer surfaces, to the entrance window 33 of a photomultipler 34.

The cylindrically lenticular scintillator 30 is preferably housed in a cut-away region of the detector collimator 11 facing the detector array 10, so that the reference measurement is not disturbed by scattered radiation. However, if, in practice, the overall amount of scattered radiation is found to be predictable or relatively constant when integrated over a complete scan in respect of different patients, the reference detector may be located on the patient side of the collimator 10.

The output from the photomultipler 34 of the reference detector 27, shown in FIG. 1, after amplification if necessary, is passed via a window circuit 35 to remove extraneous pulses lying outside the expected amplitude range, to a pulse count integrator 36. The output of the integrator is applied to the divisor input of a dividing circuit 43 in response to a timing signal applied via a line 38 which also resets the integrator count to zero. The transferred output from the integrator 36 represents the total dose measured by the reference detector 27 during the integration period scaled inversely by the sensitivity factor of the reference detector.

The reset timing pulses on the line 38 can, if desired, be synchronous with those applied from the timing circuit 21 to the integrators 16 and A-D converters 17 connected to the detector elements of the array 10, thus providing individual reference signals for each sample period. However, because of the relative insensitivity of the reference detector, which is characteristic of a more stable type of detector and is further increased by the requirement that the reference detector be relatively transparent, in the present embodiment the output of the reference detector 27 is integrated throughout the major part of, and preferably an entire rotational scan of the member 3.

Also in respect of the same integration period, either during the scan or later from corresponding stored data, all the digital signals representing successive integrated detector samples from each of those detector elements 28 of the array 10 which are situated behind the reference detector 27, are selected by selection means 40 from the outputs of the analog-digital converters 17 and accumulated in an accumulator register 41. When all the data acquired from the detectors 28 during a rotational scan, has been accumulated, a timing signal on the line 38 causes the total to be applied to the divided input of the dividing circuit 43, and the register 41 to be reset.

This manner of operation assumes an equal weighting for each detector 28 and implies that the reference detector is equally sensitive to radiation throughout its width. Since the scintillator 30 is lenticular in cross-section, the sensitivity will, in general, vary with measurement path position along the array 10. The effect of this can be taken into account by suitably weighting the contributions made by the individual backing detectors 28 to the accumulated total in the accumulator 41. Thus each input sample from a detector 28 near either edge of the scintillator 30 would be multiplied by a weighting factor less than unity before accumulation, while input samples from intermediate detectors 28 would be accumulated without modification.

Once the outputs from the accumulator 41 and pulse count integrator 36 have been transferred, the dividing circuit 43 is actuated to form the ratio of the accumulated total from the backing detectors 28 to the integrated total from the reference detector 27 during the rotational scan. Since both signals are derived from the same radiation, they represent the same total dose value at that point along the array, and the ratio will represent the ratio of the actual mean sensitivity of the group of backing detectors 28 to that of the reference detector 27.

It will be apparent that the respective outputs from the pulse count integrator 36 and from the accumulator 41 can, if desired, each be logarithmically converted by log converters 37, 42 before application to the dividing circuit 43 whose function would then consist of subtraction in order to form the logarithm of the sensitivity ratio. This log value can then be used directly and conveniently in subsequent computation.

The output from the dividing circuit 43 is applied to a further detector sensitivity correction block 44.

In operation the present embodiment is employed in the following manner. Initial calibration is performed as hereinbefore described with the addition that in respect of the scan performed on the standard phantom, the corresponding ratio, or log ratio relating the sensitivity of the reference detector 27 to the mean sensitivity of the group of backing detectors 28, is formed.

The calibration process also enables the actual sensitivity values of the backing detectors 28 to be determined. These values are then combined to form a mean sensitivity value for the groups of backing detectors 28 which corresponds to that implied by the process of accumulating detector data in the accumulator 41. In other words, either by taking the arithmetic mean of the sensitivities of the individual detectors 28 for equal contributions, or by forming a suitably weighted means in the case of a weighted contribution.

The mean backing detector sensitivity is then suitably multiplied by the sensitivity ratio to give the reference detector sensitivity which is stored for use to correct later measurements.

When measuring path attenuation in a body section 1 of a body under examination, the sensitivities of the high efficiency detector elements of the array 10 will tend to drift significantly so that for each measurement, corresponding detector sensitivity comparison chains are set up as hereinbefore described. Each such comparison chain can involve the successive comparisons of as many as thirty detector pairs, and this can give rise to a cumulative error.

FIG. 4 illustrates the measurement of an attenuation profile by the detector array 10 across the fan beam, in the presence of the normal fixed attenuator 29 (correction wedge), and for the sake of explanation, a uniformly attenuating body section 1.

The outer radial boundary about the rotation centre 6, of the wedge attenuation field of the fixed attenuator 29, as indicated in FIG. 4a by the circle 50 outside which the measured attenuation profile 51, shown ideally in FIG. 4b, is constant, and within which the attenuation 52 is reduced smoothly towards the projection of the rotation centre 6, so that, in the presence of a body of uniform attenuation equal to that of water, the overall range of intensities which have to be measured by the detectors of the array 10, is thereby reduced.

An ideal profile of measured attenuation values relating to a body section 53 of uniform density, is indicated by the solid line 54 in FIG. 4b.

FIG. 4c illustrates by the graph 55, an attenuation profile resulting from the application of a detector sensitivity comparison chain correction process to the detector signals from the array 10 with reference to the sensitivity of the terminal detector 25. An accurate value for the attenuation at the centre of the array is indicated by the point 27', and, in general, this will differ by an amount B from the attenuation value 28' derived using the chain-corrected sensitivity values relating to the detectors 28.

In accordance with the present embodiment, a measure of the difference value B between the reference attenuation value 27', and the attenuation value 28' which is measured by the detectors 28 and therefore depends on the chain corrected sensitivity values determined for those detectors, is established in the course of a measurement as follows. The ratio of the sensitivity of the reference detector 27 to the mean sensitivity of the group of backing detectors 28, is determined, as hereinbefore described, from measurement data acquired during a rotational measurement scan of the member 3. The stored sensitivity value of the reference detector, determined during the initial calibration, is then recalled and multiplied by the inverse of the sensitivity ratio relating to the measurement scan to provide a correct reference value for the mean (or weighted mean) sensitivity value of the group of backing detectors 28.

The corresponding mean (or weighted mean) value of the chain-corrected sensitivities of the backing detectors 28 relating to the measurement data, is then formed and subtracted from the said correct reference value to provide an error correction value representing the difference B. The stored chain-corrected sensitivity values relating to the part of the detector array 10, are then corrected by applying a progressively increasing amount (proportion) of this correction value to the stored value of each successive detector along the array 10, starting with a zero correction for that of the terminal detector 25 which establishes the correct sensitivity at the beginning of the comparison chain, to the entire correction value for the last detector 28 at the end of the comparison chain.

The correction value can be distributed among the various detector sensitivity values in various ways. For example, if the actual sensitivity values are used the correction can be distributed in the form of an arithmetical progression, while if log sensitivity values and a log correction value are employed for computational purposes the distribution can take the form of a geometrical progression by adding progressive fractions of the log correction value to successive stored detector log sensitivities. A disadvantage of working with log values is that individual log detector sensitivity values would have to be converted via an antilog converter to form the arithmetic mean or weighted mean value.

In the present embodiment of the invention, however, a preferred method of distributing the error correction value between the various detectors of the array, is carried out in accordance with the integral of the modulus of the slope of the attenuation profile relating to the set of measurements. This is illustrated by the graphs shown in FIGS. 4d and 4e with reference to the attenuation profile 55, shown in FIG. 4c.

The attenuation profile 55, is first computed in conventional manner from the respective outputs and chain-corrected sensitivities of the detectors of the array 10, and the intensity Io of the source. The slope of the profile 55 is then determined computationally by differentiating with respect to detector position along the array, and the modulus taken to generate the profile 56 shown in FIG. 4d.

The profile 56 is then integrated starting from the end associated with the terminal detector 25 to form a profile 57 (FIG. 4e), and the final integral value B' of the integral, is then related to the error correction value derived from the difference between the actual and chain-corrected detector sensitivities, represented as log values, to form a scaling factor $\alpha$ such that $\alpha$ B' is equal to the error correction value.

The profile 57 will, in fact, comprise a sequence of stored individual digital values, each related to a corresponding detector of the array 10 starting from the terminal detector 25 and ending at the detector 28 forming the end of the comparison chain. The profile 57 is multiplied by the scaling factor $\alpha$ and each resultant scaled digital value is added or subtracted from the chain-corrected sensitivity value relating to the corresponding detector element depending on the sign of the difference, e.g. representative of B, between the chain-corrected mean sensitivity and the actual mean sensitivity measured relative to that of the reference detector 27. In effect the scaled profile 57 is added or subtracted to the detector sensitivity values so that the curve 55 of FIG. 3c passes through the reference point 27' at 28' after the attenuation values have been recomputed from the stored detector measurement signals using the further corrected detector sensitivity values.

The described method of distributing the correction has the advantage that the largest amount of relative correction is applied at positions along the array 10 at which consistent errors are most likely to occur in the chain-correction process, namely at points where the measurement signal changes most rapidly with respect to detector position along the array.

While an embodiment has been described using only one reference detector located in front of the central portion of the array 10, a plurality of reference detectors may be used uniformly spaced across the front of the array 10 between the terminal detectors 25 and 26, and the sensitivity of each reference detector would be related in the manner described herein to the mean sensitivities of detector elements of the array 10 which receive substantially the same radiation throughout the integration period.

When more than one reference detector 27 is employed across the array 10, the normal detector comparison chains are established using corresponding terminal detectors as initial reference points and ending at the centre of the array followed by an adjustment of the correction chains for any discrepancy at the centre. The correction chains are then divided into spans from one reference detector to the next. The hereinbefore described further correction in accordance with the invention being applied first to a span starting at a terminal detector 25, 26, and ending at the first reference detector. The next span to the next reference detector is then corrected in similar manner after adding (or subtracting) the correction α B' applied at the end of the first span to all the stored sensitivity values of the second span. From this second starting point, it is possible that the error at the end of the second span may be of opposite sign indicating an opposite correction. The process is continued until all the detectors of the array 10 have been corrected relative to the corresponding reference detector related values.

The integration period for the reference measurement may be made less than an entire scan, but if it is made too short not only will the lower sensitivity of the reference detector introduce a significant noise element into the comparison, but it may then become necessary to weight the chain-corrected sensitivities forming the comparison mean by individual factors representing the relative amount of radiation received by each detector during the integration period. This is because a short integration period will allow a greater amplitude of higher spatial frequencies to be present affecting the final result.

In the described embodiment, the outputs from all the detectors 28 of the array 10 which lie behind the reference detector 27 are combined to form the reference comparison. However, provided that integration is effected over the entire rotational scan, or at least a major part thereof, and the body section under examination does not contain any unusual anomalies of density distribution, a useful amount of correction can be provided by integrating the output from only one of the detectors 28, preferably that situated in the centre of the region covered by the reference detector 27. This would simplify calculation, and depends on forming the average of the path attenuation measured by one detector throughout the whole or major part of the scan. This effectively removes the higher spatial frequencies from the detector measurement profile and means that the total dose measured by closely adjacent detectors 28 would be similar enabling the overall measurement made by one detector 28 to be regarded as representative of that which would be made by the others. This would avoid the need of averaging or weighting the group of chain-corrected sensitivites in forming the error correction difference value, possibly at the expense of correction performance with some subjects.

The reference detector can comprise other forms of detector provided the requirements of good long term stability and linearity are satisfied. For example, a sodium iodide crystal can be employed as the scintillator, or an ionisation detector employing, for example xenon, provided that the reference detector passes a useful amount of radiation on to the detector array 10, and that the reference detector components, for example the electrodes or envelope of an ionisation detector, do not cast a hard shadow of significant extent on the detector array 10.

I claim:

1. In computed tomography apparatus for measuring the attenuation of penetrating radiation along each of a plurality of measurement paths in the plane of a predetermined planar section of a body under examination and computing therefrom the distribution of local attenuation in the body section, including: a source of penetrating radiation arranged to irradiate the body section with a fan-shaped beam coplanar with the body section; an array of detectors arranged to receive said radiation after it has passed through the body section, the array extending so that a terminal detector thereof receives direct radiation from the source unattenuated by the body section, the source and detectors being displaceable relative to one another so that radiation from a respective measurement path in the body section can be measured in succession by different detectors of the array; and signal processing means arranged to receive measurement signals from the detectors, which compare signals provided by different detectors of the array from a measurement of radiation along substantially the same respective measurement path in the body section to determine the sensitivity of a detector relative to that of another and to repeat the comparison in respect of an overlapping succession of respective pairs of detectors to determine and correct the sensitivities of at least one calibration sequence of detectors along the array in a pair-wise succession relatively to a said terminal detector, the improvement wherein, said apparatus comprises:

at least one reference detector which is substantially transparent to said penetrating radiation and is located in the path of said radiation which has passed through the body section and in front of at least one intermediate detector of said array; said signal processing means further functioning to compare the signal provided by said reference detector(s) with that provided by at least one corresponding intermediate detector of the array which is part of said calibration sequence and receives radiation which has passed through said reference detector, to generate therefrom a corresponding correction signal representative of cumulative correction error present in the relevant span of the calibration sequence, and to distribute related corrections in respect of the detectors forming said span of the calibration sequence.

2. Apparatus as claimed in claim 1, wherein the source and detector array rotate about the body during a measurement and the signal processing means integrate respective outputs from said reference detector and from at least said intermediate detector of the array which receives radiation which has passed through the reference detector throughout at least a major portion of a rotary measurement scan, form the ratio of the resultant integrals, form the product of said ratio and a stored value which represents the sensitivity of the reference detector to generate a measured sensitivity value representative of the sensitivity or mean sensitivity of said intermediate detector(s), and determine the difference between said measured sensitivity value and an initially-corrected sensitivity value which are correspondingly representative of the sensitivity or mean sensitivity of said intermediate detector(s) as initially corected using said calibration sequence to provide said correction signal representative of a cumulative error present in the relevant span of the calibration sequence.

3. Apparatus as claimed in claim 2, wherein the reference detector extends along the detector array in front of a backing group of said intermediate detectors and the signal processing means weights respective outputs of said backing group with respect to said integration, and correspondingly weights the respective detector sensitivities as initially corrected using said calibration sequence prior to forming said initially-corrected sensitivity value therefrom, the weightings respectively applied with respect to each said intermediate detector being dependent on the sensitivity of the reference detector to said radiation passing therethrough along the corresponding measurement path defined by the intermediate detector, relative to the sensitivity thereof with respect to a measurement path passing centrally therethrough.

4. Apparatus as claimed in any one of the preceding claims wherein the signal processing means computes a distribution function comprising the integral of the modulus of the slope of a path-attenuation profile generated from detector output signals and a set of corresponding detector sensitivity values as initially corrected using a said calibration sequence, and then derives said related corrections from said correction signal representative of a cumulative correction error present in the relevant span of the calibration sequence and distributes said related correction among the detectors forming the relevant span of the calibration sequence in accordance with said distribution function, the value of said distribution function being zero at an end of the relevant span which coincides either with a terminal detector or a further corrected detector sensitivity value which forms the end of a previously processed, correct span.

5. Apparatus as claimed in any one of claims 1–3 wherein each reference detector comprises a scintillator, a photocell optically coupled to the scintillator, and means which integrate the output signal of the photocell by counting scintillation pulses generated by the detector.

6. Apparatus as claimed in claim 5, wherein the scintillator comprises a plastic scintillator and the photocell comprises a photomultiplier.

7. Apparatus as claimed in claim 5 wherein the scintillator extends transversely across the front of the detector array and has a convex lenticular cross section in the longitudinal direction of the detector array.

8. Apparatus as claimed in any one of claims 1 to 3 wherein the reference detector comprises an ionisation detector.

9. Apparatus as claimed in any one of claims 1 to 3 wherein the source of penetrating radiation comprises an X-ray tube and means for deflecting an electron beam over the surface of a target anode of the tube to thereby displace an electron impact spot and hence an effective source position relative to the X-ray tube and the detector array.

10. Apparatus as claimed in claim 4 wherein the source of penetrating radiation comprises an X-ray tube and means for deflecting an electron beam over the surface of a target anode of the tube to thereby displace an electron impact spot and hence an effective source position relative to the X-ray tube and the detector array.

* * * * *